United States Patent [19]

Schneider et al.

[11] Patent Number: 4,547,599
[45] Date of Patent: Oct. 15, 1985

[54] PROCESS FOR SCAVENGING FREE CHLORINE IN AN ETHYLENE DICHLORIDE STREAM

[75] Inventors: Wolfgang Schneider, Broadview Heights; John P. Lenczyk, Akron, both of Ohio

[73] Assignee: The B. F. Goodrich Company, Akron, Ohio

[21] Appl. No.: 604,565

[22] Filed: Apr. 27, 1984

[51] Int. Cl.$^4$ ............................................. C07C 17/06
[52] U.S. Cl. ................................. 570/241; 570/254; 570/262; 204/163 R
[58] Field of Search .................. 570/254, 262, 241; 204/163 R

[56] References Cited

U.S. PATENT DOCUMENTS 3,629,085 12/1971 Coppens .......................... 204/163 R
4,347,391 8/1982 Campbell ............................ 570/254

FOREIGN PATENT DOCUMENTS 674550 11/1963 Canada ................................. 570/254

Primary Examiner—Charles F. Warren
Assistant Examiner—Joseph A. Boska
Attorney, Agent, or Firm—Alfred D. Lobo; Alan A. Csontos

[57] ABSTRACT

A trace amount of free chlorine, present along with comparable amounts of ethylene, oxygen and water vapor in the ethylene dichloride (EDC) effluent from a direct chlorination reactor, may be effectively scavenged by exposing the effluent to ultraviolet ("u-v") light having a wavelength less than about 4000Å which is absorbed by the chlorine, but to which both ethylene and EDC are essentially transparent. In this process, contaminant chlorine in substantially pure (99.+%) EDC is catalytically activated and reacts with EDC to form an unwanted byproduct, namely 1,1,2-trichloroethane ("triane"). The process is effective in either the gaseous phase or the liquid phase.

4 Claims, 3 Drawing Figures

PROCESS FOR SCAVENGING FREE CHLORINE IN AN ETHYLENE DICHLORIDE STREAM

BACKGROUND OF THE INVENTION

This invention relates to scavenging trace amounts of chlorine in ethylene dichloride ("EDC") generated by the reaction of chlorine and ethylene. This reaction is the basis for the well-known "direct chlorination of ethylene" in the widely used commercial catalytic process for the production of EDC. The reaction rate is controlled by mass transfer, with absorption of ethylene as the limiting factor whether the reaction is carried out with a slight excess of ethylene, or alternatively chlorine, fed to the reactor. The heat of reaction is dissipated either through conventional water cooling of a typical low temperature direct chlorination reactor operating in the range from about 50° C. to about 65° C., or, by operating the reactor at the boiling point of EDC under pressure up to about 50 psig, hence referred to as a "boiling reactor". The boiling reactor is a particular type of direct chlorination reactor.

Though it has long been known that the effluent from a boiling reactor is highly corrosive, it was only recently found that the main cause of such corrosion was the presence of free chlorine and trace quantities of moisture. We do not know of any prior art directed to minimizing the concentration of free chlorine in the vent gases from a boiling reactor.

We are well aware that the problem of minimizing corrosion due to the effluent, without specific regard as to minimizing the production of free chlorine, has confronted many persons skilled in the art. Corrosion is pronounced even at room temperature; it gets exponentially worse, doubling for every 10° C. increase, so that in the range above 50° C. it is in full effect; and, if one wishes to operate a commercial boiling reactor, one cannot avoid operating in the elevated temperature range. To minimize corrosion in such a manner as to provide an effluent which is not only acceptably corrosive but economically not unduly burdensome is a difficult problem to which a better solution is constantly sought. Part of the difficult lies with the varied considerations which define the problem, as it presents itself in different guises, hence the elusiveness of the solution; and by no means a minor part lies in the unforgiving economics of any solution to the problem. It is axiomatic that solutions to industrial problems must be economically acceptable.

As is well known, the economics of chemical engineering unit operations in the production of EDC of vinyl chloride monomer are such that, optimally, the ethylene and chlorine are converted to EDC without the formation of unwanted byproducts and most important, without leaving any free chlorine residue in the effluent. The problem of corrosion is discussed in "Alloy Selection for VCM Plants" of Schillmoller, C. M., *Hydrocarbon Processing* pg 89–93, March 1979.

In practice the reaction is controlled so that carbon steel equipment may be used. The problem is that as little as from about 100 parts per million (ppm) to about 5000 ppm (0.5%) by weight (by wt) of free chlorine, has a highly corrosive effect on downstream equipment when trace amounts of water are present in the effluent as a contaminant. The problem has been countered in the past by washing and neutralizing the effluent with aqueous alkali but this generates an alkali metal salt. Further complications arise due to poisoning of catalyst due to the presence of alkali in subsequent processing steps, and to the relatively high solubility of halogenated hydrocarbons in the alkali wash, which complication is exacerbated by the large volume of the wash required to be circulated. Then to dry the washed EDC was an undesirable cost.

From the viewpoint of fluid handling, not to mention energy utilization, the solution to the problem was economically onerous and technically inelegant. It was decided to concentrate on removal of chlorine without alkali washing the reaction products, and to do so as soon after they leave the direct chlorination reactor as possible. Further, it was decided not to be concerned with the entrainment of ferric chloride ($FeCl_3$) catalyst, relying on controlling reaction conditions sufficiently to entrain only a minimal and acceptable level in the effluent from the boiling reactor.

It is kown that ethylene chloride (EDC) reacts with chlorine to produce 1,1,2-trichloroethane ("triane") in the presence of ultraviolet ("u-v") light as taught in U.S. Pat. No. 2,174,737, when from 0.2 to about 1.0 mol of chlorine per mol of EDC is present in the liquid phase. However, not only is this reaction inhibited by the presence of oxygen, it requires that a relatively large molar amount of chlorine relative to ethylene be present if the reaction is to produce triane.

In the boiling reactor, whether it is run with a slight excess of chlorine or ethylene, the main byproduct is triane which probably forms through radical reactions beginning with homolytic dissociation of a small fraction of the chlorine. However, oxygen which is deliberately introduced as an impurity with the chlorine, tends to increase selectivity to EDC by inhibition of free radical reactions that produce triane (see Kirk & Othmer, supra).

Because the formation of triane is deemed undesirable in the direct chlorination of ethylene where EDC is the desired product, its formation is suppressed by the oxygen, usually supplied as injected air (see *Encyclopedia of Chemical Technology*, Kirk & Othmer, Third Edition, Vol. 23, pg 871, Wiley Interscience 1984).

Since the concentration of free chlorine and ethylene are each so low relative to the EDC generated, whether in the liquid phase of a low temperature reactor, or in the effluent vapor phase as the reaction products leave the boiling reactor, or in the liquid phase after the effluent is condensed, it seemed unlikely that the chlorine and ethylene would react. It would simply be difficult for the chlorine and ethylene molecules to find each other with all the EDC present. It just did not occur to us to tray and react the free chlorine and EDC to produce triane, the formation of which we were deliberately suppressing. Moreover, the amount of oxygen present is relatively high in relation to the chlorine and ethylene and would likely inhibit the production of triane.

SUMMARY OF THE INVENTION

It has been discovered that a trace amount of free chlorine present along with comparable amounts of ethylene, oxygen and water vapor in the EDC effluent from a direct chlorination reactor, may be effectively scavenged by exposing the effluent to ultraviolet ("u-v") light having a wavelength less than 4000 Å which is absorbed by the chlorine, but to which both ethylene and EDC are essentially permeable, that is, transparent.

It is therefore a general object of the invention to provide an elegant and effective process for scavenging contaminant chlorine in substantially pure (99.+%) EDC by catalytically activating and reacting the chlorine with EDC to form an unwanted byproduct, namely 1,1,2-trichloroethane ("triane"), in the presence of u-v light having a wavelength in the range from about 2000 Å to about 4000 Å.

It is a specific object of this invention to expose the gaseous effluent from a boiling reactor, which effluent is contaminated with free chlorine, ethylene, oxygen and water vapor, to u-v light in the aforesaid wavelength range, at a temperature in the range from about 65° C. to about 120° C., at a pressure in the range from about 1 atmosphere (atm) to about 3 atm, for a period of time from about 1 min to about 1 hr so as to reduce the chlorine contamination to a level below 50 ppm. This reaction may also be carried out with the gaseous effluent from a product distillation column in which EDC is purified.

It is another specific object of this invention to expose liquid effluent from a direct chlorination reactor to u-v light in the aforesaid wavelength range generated by lamps directed towards the interior of a tank in which the liquid is held at a temperature in the range from about 30° C. to about 60° C., and elevated pressure.

BRIEF DESCRIPTION OF THE DRAWINGS

The foregoing and other objects and advantages of this invention will appear more fully from the following description, made in connection with the accompanying drawing schematically illustrating a preferred embodiment of the invention, in which drawing.

DETAILED DESCRIPTION OF PREFERRED EMBODIMENTS

This invention is described in particular relation to a direct chlorination reactor which is a boiling reactor, it being understood that the invention is equally applicable to any direct chlorination reactor in which the reaction of chlorine and ethylene produces a substantially pure (99.+%) EDC effluent containing from about 100 ppm to about 0.5% by wt of chlorine, and small amounts of ethylene, oxygen and water vapor.

Figure 1:
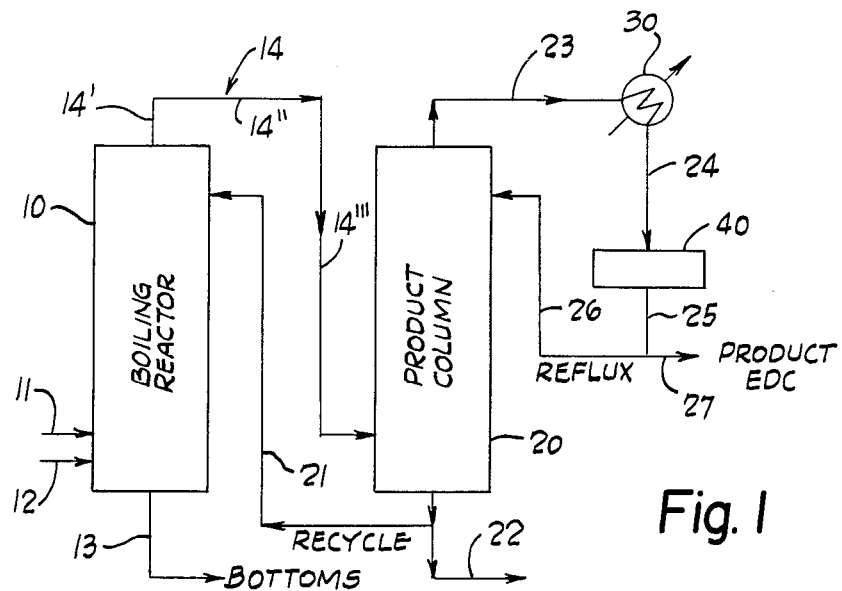
FIG. 1 is a simplified schematic flow diagram illustrating the relationship of a typical boiling reactor and a product column, and the flow of effluents from each, in a conventional vinyl chloride monomer ("VCM") plant.

Referring to the drawing, and particularly to FIG. 1, there is shown a schematic flow diagram of a boiling reactor 10 in which liquid EDC and a catalytic amount of $FeCl_2$ is held under elevated pressure from about 1 atm to about 3 atm, at its boiling point. A slight molar excess of ethylene, about 5% over the stoichiometric amount of chlorine required to form EDC, is fed to the reactor through an ethylene feed line 11, and chlorine is fed through a chlorine feed line 12, both near the bottom, so that they react exothermically within the hot liquid EDC. The heat of reaction boils off EDC and the reaction is controlled so that the reaction mass is maintained at a temperature in the range from about 50° C. to about 120° C., and more preferably in the range from about 50° C. to about 95° C.

The chlorine is deliberately "doctored" with oxygen present in the range from about 0.1% to about 1% by wt of the combined flow of ethylene chlorine and oxygen, to increase the selectivity to EDC and to inhibit the free radical reactions which produce triane and other polychlorinated compounds having more than two (2) Cl atoms in each molecule. Though such polychlorinated compounds are undesirable, they are nevertheless unavoidably formed as byproducts of the reaction, but being higher boiling than EDC, tend to concentrate in the reaction mass. Therefore, a bottoms stream 13 is withdrawn from the reactor. The oxygen is conveniently introduced by injecting air into either the ethylene or the chlorine feed lines, each of the gases being thoroughly dried over a bed of dessicant to remove moisture.

Alternatively, the reaction in the boiling reactor may be carried out with a slight molar excess of chlorine, in the range from about 2 to about 8% over stoichiometric. Whether the reaction is carried out with an excess of ethylene, or an excess of chlorine, there is always present a deleterious amount of contaminant chlorine. Further, despite attempts to provide all the reactants in as dry a form as practical, there is always present a small amount of moisture in the range from about 20 ppm to about 0.1%.

The effluent leaves the reactor near the top through effluent line indicated generally by reference numeral 14, and is led into a product column 20 near its bottom. The product column is a distillation column fitted with trays or other conventional vapor-liquid equilibria staging means (not shown). A portion of the bottoms from the product column is recycled to the boiling reactor through a recycle line 21 by a recycle pump (not shown) the remainder being withdrawn through bottoms line 22.

The overhead of the product column leaves through overhead line 23, is cooled in a condenser 30, and commercially pure liquid EDC (99.5+%) flows through line 24 and collected in condensate tank 40. This product EDC is withdrawn through line 25, a portion being refluxed through line 26 to near the top of the product column, the remainder being pumped through line 27 to product storage.

Figure 2:
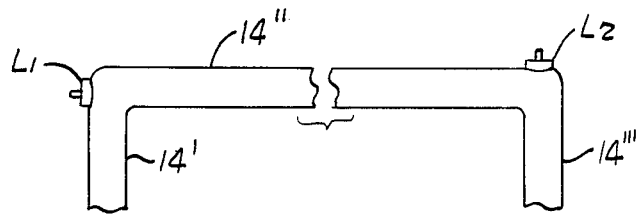
FIG. 2 is a detail schematically illustrating how u-v lamps are positioned to direct their light longitudinally through the effluent lines carrying vapor.

Referring to FIG. 2 there is schematically illustrated a detail, with portions broken away, of line 14 in which u-v lamps $L_1$ and $L_2$ are mounted. The first lamp $L_1$ is mounted in the elbow connecting portions 14' and 14" of the line 14, so that the u-v light is beamed longitudinally axially through horizontal portion 14". The second lamp $L_2$ is mounted in the elbow between portions 14" and 14''' so that its u-v light is beamed longitudinally axially and generally vertically through portion 14'''. In each case, the lamps are positioned to afford the maximum exposure time in the lines.

The effluent in line 14 is substantially pure EDC contaminated in line 14' with from about 100 ppm to about 0.5% by wt of chlorine, and from 100 ppm to about 0.5% of oxygen, with comparable amounts less than 1% by wt of polychlorinated compounds. The amount of ethylene may be somewhat larger, generally in the range from about a 0.1% to about a 5% molar excess, though the amount of this excess is not narrowly critical.

Irradiation of the effluent in lines 14" and 14''' reduces the concentration of chlorine. In an analogous manner, u-v lamps may be mounted in the overhead product line 23. The decrease in concentration of chlorine is a function of the intensity of the u-v light and the time of irradiation. It will be recognized that, though line 14 is schematically illustrated as having only a single horizontal portion 14', the requirements of exposure time may dictate several traverses of line each with its own irradiation means. The same arrangement may be made for line 23.

Figure 3:
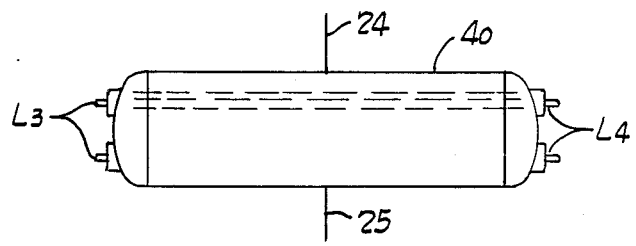
FIG. 3 is a detail schematically illustrating how u-v lamps are positioned to direct their light through liquid effluent held in a condensate tank.

Referring now to FIG. 3, there is schematically illustrated a detail of condensate tank 40 in which commercially pure liquid EDC is held. The tank is fitted with plural u-v lamps $L_3$ and $L_4$ on opposite sides of the tank so that substantially the entire contents of the tank are uniformly irradiated while held therewithin. The number of lamps used will depend upon the size of the tank and the intensity of the lamps. The lamps are positioned in chambers shielded by u-v permeable windows. Cool water is circulated through the chambers to cool the lamps.

The u-v lamps used are commercially available lamps having a wavelength less than 3800 Å the major portion of the wavelength being in the range from about 2000 Å to about 3800 Å, to which EDC is transparent but chlorine is not, whether in the gaseous or the liquid phase. In the liquid phase it is thought that the chlorine contaminant is dissolved in the EDC, as is the unreacted ethylene. The u-v light provides free radicals which activate the free chlorine and catalyze the formation of triane, generally in preference to the reaction of chlorine with ethylene. This is established by measurements which indicate that the concentration of ethylene does not change significantly, that of chlorine decreases, and that of triane increases.

As would be expected, the catlaytic, effectiveness of the u-v light will also depend upon its intensity, though this is not narrowly critical in carrying out the reaction if time of reaction is of little concern. From a practical point of view it will be appreciated that the reaction scavenging chlorine must be completed within a relatively short time in the range from about 1 min to about 30 min, and the intensity of the light from the lamps will be chosen to scavenge the predetermined amount of chlorine within such time.

In the following three examples, the effectiveness of scavenging free chlorine in the effluent from a typical boiling reactor, by exposure to u-v light is demonstrated with samples of EDC containing (a) 0.28%, (b) 0.19% and (c) 35 ppm of chlorine, respectively. These concentrations are representative of the chlorine content of EDC in the reflux drum 40 of the product column 20.

Each batch experiment with samples (a)-(c) was run in a 4" diameter glass column surrounded with six 40 watt u-v lamps having the major portion of the wavelength in the range from 2500 Å to about 4000 Å. The charge in each example was 2 liters and the analyses were made about every two min.

In each example, the disappearance of chlorine followed a zero order reaction with a rate constant of about 0.01 g moles/liter min. In each example (a) and (b) the level of chlorine was decreased to less than 50 ppm after 10 min. In the example (c) with the relatively low initial concentration of 35 ppm, the conc. of chlorine was reduced to less than 10 ppm after 10 min.

We claim:

1. In a method for producing essentially pure ethylene dichloride by the direct chlorination of ethylene in the presence of a ferric chloride catalyst in which method effluent from the reactor consists essentially of contaminated ethylene dichloride with contaminant amounts of chlorine, ethylene, oxygen and polychlorinated compounds each of said amounts being less than 0.5% by weight of the combined material flowed to said reactor, the improvement comprising,
   (a) maintaining a contaminant amount of chlorine in said contaminated ethylene dichloride in the range from about 100 ppm to about 0.5%; ethylene in the range from about 500 ppm to about 1.0%; said polychlorinated compounds in the range from about 50 ppm to about 0.1%; and oxygen in the range from about 0.1% to about 5% by weight based on the weight of the combined material flowed through said reactor, a temperature of reaction in the range from about 30° C. to about 120° C. and a pressure in the range from about 1 atm to about 5 atm; and,
   (b) exposing said contaminated ethylene dichloride to ultraviolet light having a wavelength less than about 4000 Å and a major portion in the range from about 2500 Å to about 4000 Å, to catalyze the reaction of chlorine with ethylene dichloride to form 1,1,2-trichloroethane in from about 1 min to about 40 min;

whereby said amount of chlorine after irradiation of said contaminated ethylene dichloride is present in the range from about 1 ppm to about 20 ppm.

2. The method of claim 1 wherein said amount of ethylene in said contaminated ethylene dichloride remains substantially constant.

3. The method of claim 1 wherein said reaction is carried out in the gaseous phase.

4. The method of claim 1 wherein said reaction is carried out in the liquid phase.

* * * * *